(12) United States Patent
Takei et al.

(10) Patent No.: US 10,123,947 B2
(45) Date of Patent: *Nov. 13, 2018

(54) DENTAL CEMENT

(71) Applicant: KURARAY NORITAKE DENTAL INC., Kurashiki-shi (JP)

(72) Inventors: Mitsuru Takei, Yokohama (JP); Yamato Nojiri, Tainai (JP)

(73) Assignee: KURARAY NORITAKE DENTAL INC, Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,458

(22) PCT Filed: Jun. 10, 2015

(86) PCT No.: PCT/JP2015/002915
§ 371 (c)(1),
(2) Date: Dec. 9, 2016

(87) PCT Pub. No.: WO2015/190100
PCT Pub. Date: Dec. 17, 2015

(65) Prior Publication Data
US 2017/0135909 A1 May 18, 2017

(30) Foreign Application Priority Data
Jun. 10, 2014 (JP) .................. 2014-119596

(51) Int. Cl.
| A61K 6/083 | (2006.01) |
| A61K 6/00  | (2006.01) |
| A61L 24/00 | (2006.01) |
| A61L 24/04 | (2006.01) |

(52) U.S. Cl.
CPC ........... *A61K 6/0023* (2013.01); *A61K 6/00* (2013.01); *A61K 6/083* (2013.01); *A61L 24/001* (2013.01); *A61L 24/043* (2013.01)

(58) Field of Classification Search
None
See application file for complete search history.

(56) References Cited

U.S. PATENT DOCUMENTS

| 5,300,537 A * | 4/1994 | Muller ................ A61L 24/06 433/228.1 |
| 5,741,543 A * | 4/1998 | Winslow .............. C09J 4/06 427/208.4 |
| 6,953,832 B2 * | 10/2005 | Moszner ............. A61K 6/0017 106/35 |
| 2002/0143138 A1* | 10/2002 | Moszner ............. A61K 6/0017 528/310 |
| 2005/0009946 A1* | 1/2005 | Oguri .................. A61K 6/0023 522/184 |
| 2005/0049326 A1* | 3/2005 | Park .................... A61K 6/083 523/118 |

FOREIGN PATENT DOCUMENTS

| JP | 3-204846 A | 9/1991 |
| JP | 11-500152 A | 1/1999 |
| JP | 2002-212019 A | 7/2002 |
| JP | 2003-96122 A | 4/2003 |
| JP | 2008-189579 A | 8/2008 |
| JP | 2008-260753 A | 10/2008 |
| JP | 2013-209341 A | 10/2013 |
| WO | 96/24644 A1 | 8/1996 |

OTHER PUBLICATIONS

International Search Report dated Aug. 25, 2015 in PCT/JP2015/002915 filed Jun. 10, 2015.
Extended European Search Report dated Jan. 4, 2018 in Patent Application No. 15806848.6, citing document AA therein 10 pages.

*Primary Examiner* — Peter A Salamon
(74) *Attorney, Agent, or Firm* — Oblon, McClelland, Maier & Neustadt, L.L.P.

(57) ABSTRACT

The present invention provides a dental cement that exhibits excellent adhesiveness to dentin and has high mechanical strength. The present invention relates to a multi-part dental cement containing: an asymmetric acrylamide-methacrylic acid ester compound (a); an acid group-containing (meth) acrylic polymerizable monomer (b); a hydrophobic cross-linkable polymerizable monomer (c); a chemical polymerization initiator (d); and a filler (e). The asymmetric acrylamide-methacrylic acid ester compound (a) is represented by the following general formula (1):

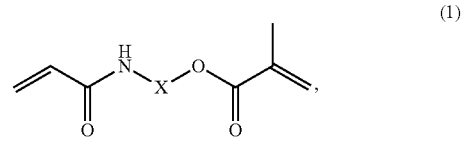

(1)

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —$NR^1$—, —CO—$NR^1$—, —$NR^1$—CO—, —CO—O—$NR^1$—, —O—CO—$NR^1$—, and —$NR^1$—CO—$NR^1$—, and $R^1$ is a hydrogen atom or an optionally substituted, linear or branched $C_1$ to $C_6$ aliphatic group.

12 Claims, No Drawings

DENTAL CEMENT

TECHNICAL FIELD

The present invention relates to a multi-part dental cement used, for example, for luting dental prostheses such as crowns, inlays, and bridges to tooth structures during dental treatment.

BACKGROUND ART

For restorative treatment of tooth structures (enamel, dentin, and cementum) damaged, for example, by dental caries, dental cements are used as materials for luting dental prostheses such as crowns, inlays, and bridges to broken or chipped tooth crowns. A dental cement is usually composed of a polymerizable monomer, a filler, and a polymerization initiator. (Meth)acrylate-based polymerizable monomers are widely used as such polymerizable monomers.

It is desirable that a dental cement have high adhesiveness to tooth structures (in particular to dentin) in order to prevent detachment of a prosthesis after restorative treatment and to prevent secondary caries. For improvement of the adhesiveness to dentin, it is considered important to allow a polymerizable monomer component contained in the dental cement to penetrate into the collagen layer of dentin and to cure therein so as to form a dentin-dental cement hybrid layer (a so-called resin-impregnated layer). The use of a hydrophilic multifunctional (meth)acrylate-based polymerizable monomer having a specific chemical structure as such a polymerizable monomer has been proposed to improve the adhesiveness of the dental cement to dentin.

On the other hand, (meth)acrylate-based polymerizable monomers have the disadvantage of being susceptible to hydrolysis during storage and thus having low storage stability. Therefore, dental materials containing multifunctional (meth)acrylamide-based polymerizable monomers have been proposed to provide dental materials having high resistance to hydrolysis.

Examples of such conventional dental materials are as follows. Patent Literature 1 proposes a composition containing a (meth)acrylate-based polymerizable monomer having at least two polymerizable groups and at least two primary hydroxyl groups, as a composition suitable for use as a dental composition (including a dental cement). Patent Literature 2 proposes a self-adhesive dental cement containing a (meth)acrylate-based polymerizable monomer having an unconjugated carbon chain with at least four singly-bonded carbon atoms, at least two polymerizable groups, and at least two hydroxyl groups.

Patent Literature 3 proposes a dental material (including a dental cement) containing two (meth)acrylamide-based polymerizable monomers: a bifunctional (meth)acrylamide-based polymerizable monomer represented by the general formula (3) having two (meth)acrylamide groups both of which are secondary amide groups; and a (meth)acrylamide-based polymerizable monomer represented by the general formula (4) having two (meth)acrylamide groups both of which are tertiary amide groups (hereinafter, in the present description, a (meth)acrylamide-based polymerizable monomer having two (meth)acrylamide groups both of which are secondary amide groups and a (meth)acrylamide-based polymerizable monomer having two (meth)acrylamide groups both of which are tertiary amide groups may be referred to as symmetric (meth)acrylamide compounds, for the sake of convenience).

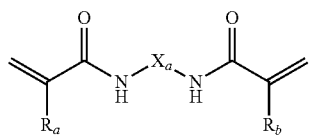

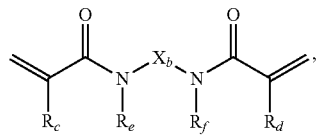

where $R_a$, $R_b$, $R_c$, and $R_d$ are each independently a hydrogen atom or a methyl group, $R_e$ and $R_f$ are each independently a group other than a hydrogen atom, such as an alkyl group or an aryl group, and $X_a$ and $X_b$ are each independently a divalent organic group optionally having an oxygen atom and a nitrogen atom.

However, the hydrophilic multifuctional (meth)acrylate-based polymerizable monomers disclosed in Patent Literatures 1 and 2 and the bifunctional (meth)acrylamide-based polymerizable monomer represented by the general formula (3) disclosed in Patent Literature 3 have the following disadvantages. Most of these polymerizable monomers are crystalline solids and must be used in combination with a large amount of a hydrophilic monofunctional (meth)acrylate-based polymerizable monomer such as 2-hydroxyethyl (meth)acrylate to obtain a homogeneous composition, and thus only a limited range of compositions can be prepared. In addition, when any of these polymerizable monomers are used in a dental cement, the resulting cured product has high water absorbency and low mechanical strength. The (meth)acrylamide-based polymerizable monomer represented by the general formula (4) is oily in nature and has good compatibility with other polymerizable monomers, but due to its low hydrophilicity, a dental cement containing this oily compound has the disadvantage of low adhesiveness to tooth structures.

CITATION LIST

Patent Literature

Patent Literature 1: JP 2008-189579 A
Patent Literature 2: JP 2008-260753 A
Patent Literature 3: JP 2002-212019 A

SUMMARY OF INVENTION

Technical Problem

It is an object of the present invention to provide a dental cement that exhibits excellent adhesiveness to dentin and has high mechanical strength.

Solution to Problem

The present invention that has solved the above-described problems is a multi-part dental cement containing: an asymmetric acrylamide-methacrylic acid ester compound (a); an acid group-containing (meth)acrylic polymerizable monomer (b); a hydrophobic crosslinkable polymerizable monomer (c); a chemical polymerization initiator (d); and a filler (e), wherein the asymmetric acrylamide-methacrylic acid ester compound (a) is represented by the following general formula (1):

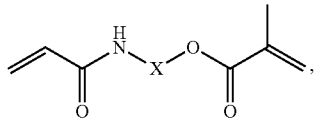

(1)

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —NR$^1$—, —CO—NR$^1$—, —NR$^1$—CO—, and —NR$^1$—CO—NR$^1$—, and R$^1$ is a hydrogen atom or an optionally substituted, linear or branched $C_1$ to $C_6$ aliphatic group.

In the multi-part dental cement, X in the above formula (1) representing the asymmetric acrylamide-methacrylic acid ester compound (a) is preferably an optionally substituted, linear or branched $C_1$ to $C_4$ aliphatic group. In the multi-part dental cement, the content of the asymmetric acrylamide-methacrylic acid ester compound (a) is preferably 2 to 50 parts by weight, the content of the acid group-containing (meth)acrylic polymerizable monomer (b) is preferably 1 to 50 parts by weight, and the content of the hydrophobic crosslinkable polymerizable monomer (c) is preferably 30 to 95 parts by weight, in 100 parts by weight of the total polymerizable monomers.

Furthermore, the multi-part dental cement may further contain a hydrophilic monofunctional polymerizable monomer (f). In the multi-part dental cement, the hydrophilic monofunctional polymerizable monomer (f) is preferably at least one selected from the group consisting of a monofunctional (meth)acrylamide-based polymerizable monomer, 2-hydroxyethyl (meth)acrylate, 2,3-dihydroxypropyl (meth)acrylate, and diacetone (meth)acrylamide, the monofunctional (meth)acrylamide-based polymerizable monomer being represented by the following general formula (2):

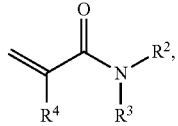

(2)

where R$^2$ and R$^3$ are each independently an optionally substituted, linear or branched $C_1$ to $C_3$ alkyl group, and R$^4$ is a hydrogen atom or a methyl group. The hydrophilic monofunctional polymerizable monomer (f) contained in the multi-part dental cement is more preferably a monofunctional (meth)acrylamide-based polymerizable monomer represented by the above general formula (2). Furthermore, when the multi-part dental cement contains the hydrophilic monofunctional polymerizable monomer (f), the content of the hydrophilic monofunctional polymerizable monomer (f) is preferably 1 to 30 parts by weight in 100 parts by weight of the total polymerizable monomers.

Advantageous Effects of Invention

According to the present invention, it is possible to provide a multi-part dental cement that exhibits excellent adhesiveness to dentin and has high mechanical strength.

DESCRIPTION OF EMBODIMENTS

First, polymerizable monomer components in the dental cement of the present invention are described. As used in the present description, "(meth)acrylate" collectively refers to acrylate and methacrylate. The same applies to similar expressions.

The present invention is characterized in that an asymmetric acrylamide-methacrylic acid ester compound (a) represented by the above general formula (1) having two polymerizable groups, one of which is a methacrylic acid ester group and the other of which is an acrylamide group as a secondary amide group is used (hereinafter, in the present description, a compound having two polymerizable groups bonded to a group represented by X, one of which is a methacrylic acid ester group and the other of which is an acrylamide group as a secondary amide group, is referred to as an "asymmetric acrylamide-methacrylic acid ester compound" for the sake of convenience).

It is not known exactly why a dental cement of the present invention containing an asymmetric acrylamide-methacrylic acid ester compound (a) exhibits high adhesiveness to dentin and has high mechanical strength. The reasons for this are probably as follows. The asymmetric acrylamide-methacrylic acid ester compound (a) used in the present invention has high hydrophilicity derived from amide protons and thus easily penetrates into the collagen layer of dentin. In addition, two polymerizable groups in the molecule of this compound (a), that is, an acrylamide group and a methacrylic acid ester group have relatively similar and balanced curing rates and thus the compound (a) exhibits sufficient curability and the penetrating cement forms a solid layer. In general, when an acrylic acid ester and a methacrylic acid ester have the same skeleton, the acrylic acid ester that has no methyl group and thus is sterically unhindered is more reactive than the methacrylic acid ester. The same applies to an acrylamide and a methacrylamide. Furthermore, the present inventors' studies have revealed that when a methacrylamide and a methacrylic acid ester have the same skeleton, the curing rate of the methacrylic acid ester tends to be higher than that of the methacrylamide. Therefore, when two polymerizable groups in the molecule are a methacrylic acid ester and a methacrylamide, the curing rate of the ester side tends to be higher than that of the amide side and thus their curing rates tend to be less balanced. Probably, in the asymmetric acrylamide-methacrylic acid ester compound (a), the curing rates between the ester side and the amide side is well balanced because an ester which is believed to have a higher curing rate is combined with a less reactive methacrylic group and an amide which is believed to have a lower curing rate is combined with a more reactive acrylic group. That is, the asymmetric acrylamide-methacrylic acid ester compound (a) can be considered as a compound having both high hydrophilicity derived from amide protons and high polymerization curability derived from two polymerizable groups having well-balanced curing rates.

For the reasons described above, a dental cement containing the asymmetric acrylamide-methacrylic acid ester compound (a) has not only high adhesiveness to dentin but also excellent mechanical strength. In addition, the asymmetric acrylamide-methacrylic acid ester-based compound (a) has an asymmetric structure and thus is less crystalline, is oily in nature, contains both an acrylamide group and a methacrylic acid ester group in the molecule, and thus has better compatibility with other polymerizable monomers.

The asymmetric acrylamide-methacrylic acid ester compound (a) used in the present invention is represented by the following general formula (1):

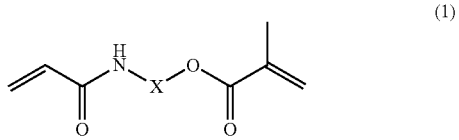

(1)

In this formula (1), X is an optionally substituted, linear or branched $C_1$ to $C_6$ aliphatic group or an optionally substituted aromatic group, and at least one linking group selected from the group consisting of —O—, —S—, —CO—, —CO—O—, —O—CO—, —NR$^1$—, —CO—NR$^1$—, —NR$^1$—CO—, —O—CO—NR$^1$—, and —NR$^1$—CO—NR$^1$— may be introduced into this aliphatic group. That is, the aliphatic group is optionally interrupted by at least one of the above-mentioned linking groups. $R^1$ is a hydrogen atom or an optionally substituted, linear or branched $C_1$ to $C_6$ aliphatic group.

X is a moiety for adjusting the hydrophilicity of the asymmetric acrylamide-methacrylic acid ester compound (a). The optionally substituted $C_1$ to $C_6$ aliphatic group represented by X may be a saturated aliphatic group (such as an alkylene group or a cycloalkylene group (for example, 1,4-cyclohexylene group)) or an unsaturated aliphatic group (such as an alkenylene group or an alkynylene group). In view of availability, ease of production, and chemical stability, it is preferable that the aliphatic group be a saturated aliphatic group (alkylene group). In view of adhesion to tooth structures and polymerization curability, X is preferably an optionally substituted, linear or branched $C_1$ to $C_4$ aliphatic group, and more preferably an optionally substituted, linear or branched $C_2$ to $C_4$ aliphatic group.

Examples of the $C_1$ to $C_6$ alkylene group include methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, tetramethylene, 1-butylethylene, 2-butylethylene, 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, 1-butylethylene, 2-butylethylene, 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene, and hexamethylene groups. The $C_1$ to $C_6$ alkylene group is preferably a methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group, and more preferably a methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group.

Examples of the optionally substituted aromatic group represented by X include an aryl group and an aromatic heterocyclic group. An aryl group is more preferred than an aromatic heterocyclic group as the aromatic group mentioned above. The hetero ring of the aromatic heterocyclic group is usually unsaturated. The aromatic hetero ring is preferably a five-membered or six-membered ring. For example, a phenyl group is preferred as the aryl group. Examples of the aromatic heterocyclic group include furan, thiophene, pyrrole, oxazole, isoxazole, thiazole, isothiazole, imidazole, pyrazole, furazan, triazole, pyran, pyridine, pyridazine, pyrimidine, pyrazine, and 1,3,5-triazine groups. Among the aromatic groups mentioned above, a phenyl group is particularly preferred.

The aliphatic group as $R^1$ may be either a saturated aliphatic group (alkyl group) or an unsaturated aliphatic group (alkenyl or alkynyl group). In view of availability, ease of production, and chemical stability, the aliphatic group is preferably a saturated aliphatic group (alkyl group). Examples of the linear or branched $C_1$ to $C_3$ alkyl group as $R^1$ include methyl, ethyl, n-propyl, isopropyl, n-butyl, isobutyl, sec-butyl, tert-butyl, n-pentyl, isopentyl, sec-pentyl, neopentyl, tert-pentyl, 1-ethylpropyl, hexyl, isohexyl, 1,1-dimethylbutyl, 2,2-dimethylbutyl, 3,3-dimethylbutyl, and 2-ethylbutyl groups. The alkyl group is preferably a methyl, ethyl, n-propyl, isopropyl, n-butyl, isobutyl, sec-butyl, tert-butyl, or the like.

$R^1$ is more preferably a hydrogen atom or an optionally substituted, linear or branched $C_1$ to $C_4$ alkyl group, and even more preferably a hydrogen atom or an optionally substituted, linear or branched $C_1$ to $C_3$ alkyl group.

When the aliphatic group as X is interrupted by the above-mentioned linking group(s), the number of the linking groups is not particularly limited. The number of the linking groups may be about 1 to 10, preferably 1, 2, or 3, and more preferably 1 or 2. In the above formula (1), it is preferable that the aliphatic group as X be not interrupted by two or more contiguous linking groups. That is, it is preferable that the linking groups be not adjacent to each other. The linking group is more preferably at least one linking group selected from the group consisting of —O—, —S—, —CO—, —CO—O—, —O—CO—, —NH—, —CO—NH—, —NH—CO—, —CO—O—NH—, —O—CO—NH—, and —NH—CO—NH—, and particularly preferably at least one linking group selected from the group consisting of —O—, —S—, —CO—, —NH—, —CO—NH—, and —NH—CO—.

The substituent in the above formula (1) is not particularly limited. For example, the substituent is preferably a halogen atom (fluorine, chlorine, bromine, or iodine atom), a carboxy group, a hydroxy group, an amino group, an amino group mono- or di-substituted by $C_1$ to $C_6$ alkyl group(s), an acyl group, an acyloxy group, an amide group, a $C_1$ to $C_3$ alkoxycarbonyl group, a $C_1$ to $C_6$ alkoxy group, a $C_1$ to $C_3$ alkylthio group, a $C_1$ to $C_6$ alkyl group, or the like, and more preferably a halogen atom (fluorine, chlorine, bromine, or iodine atom), a $C_1$ to $C_6$ alkyl group, or the like. The $C_1$ to $C_6$ alkoxycarbonyl group, the $C_1$ to $C_6$ alkoxy group, the $C_1$ to $C_6$ alkylthio group, and the $C_1$ to $C_6$ alkyl group mentioned above may be substituted by 1, 2, or 3 halogen atoms. Specific examples of the above-mentioned alkyl group are the same as those of $R^1$, and a linear or branched $C_1$ to $C_4$ alkyl group is preferred. The number of the substituents is not particularly limited. The number of the substituents may be about 1 to 8, and preferably 1, 2, or 3.

The specific examples of the asymmetric acrylamide-methacrylic acid ester compound (a) are not particularly limited, and include the following.

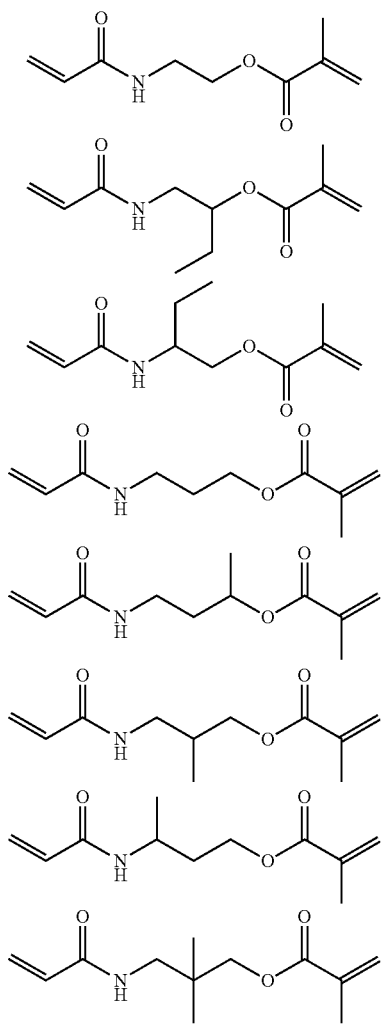

-continued

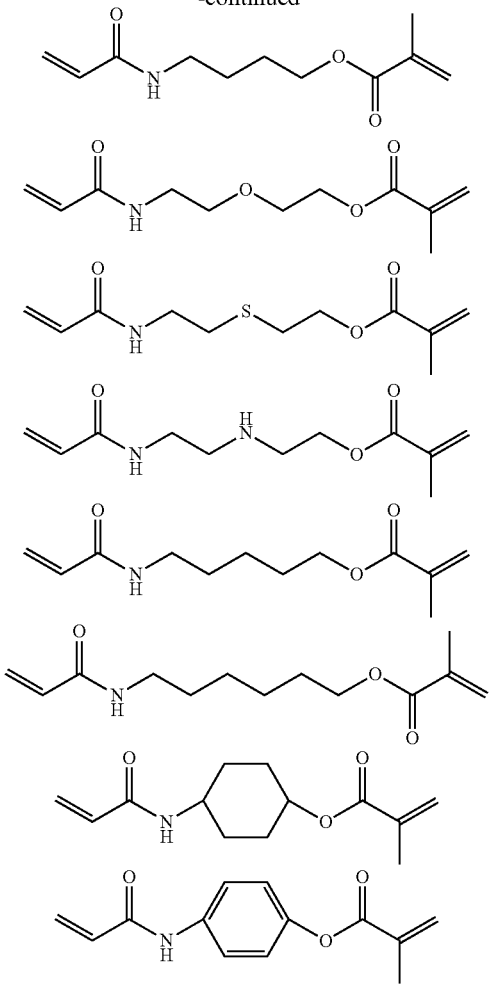

Among these, an asymmetric acrylamide-methacrylic acid ester compound having a linear or branched $C_2$ to $C_4$ aliphatic group as X is preferred in view of adhesion to tooth structures and polymerization curability. N-methacryloyloxyethyl acrylamide, N-methacryloyloxypropyl acrylamide, N-methacryloyloxybutyl acrylamide, N-(1-ethyl-(2-methacryloyloxy)ethyl) acrylamide, or N-(2-(2-methacryloyloxyethoxy)ethyl) acrylamide is more preferred. N-methacryloyloxyethyl acrylamide or N-methacryloyloxypropyl acrylamide is most preferred because of its high hydrophilicity responsible for penetration into the collagen layer of dentin.

One of the above-mentioned compounds may be contained alone as the asymmetric acrylamide-methacrylic acid ester compound (a), or a combination of two or more thereof may be contained as the asymmetric acrylamide-methacrylic acid ester compound (a). The content of the asymmetric acrylamide-methacrylic acid ester compound (a) is not particularly limited as long as the effect of the present invention can be obtained. The content of the asymmetric acrylamide-methacrylic acid ester compound (a) is preferably in the range of 2 to 50 parts by weight, more preferably in the range of 5 to 40 parts by weight, and most preferably in the range of 10 to 30 parts by weight in 100 parts by weight of the total polymerizable monomers in the dental cement.

Next, the acid group-containing (meth)acrylic polymerizable monomer (b) used in the present invention is described. In the present invention, the (meth)acrylic polymerizable monomer refers to a (meth)acrylate-based polymerizable monomer and/or a (meth)acrylamide-based polymerizable monomer.

The acid group-containing (meth)acrylic polymerizable monomer (b) is an essential component for the dental cement of the present invention to exhibit adhesiveness. The acid group-containing (meth)acrylic polymerizable monomer (b) has the effect of demineralizing tooth structures, and promotes the penetration of the asymmetric acrylamide-methacrylic acid ester compound (a) into dentin and binds to the tooth structures. The acid-group-containing (meth) acrylic polymerizable monomer (b) is a polymerizable monomer having at least one of acid groups such as a phosphoric acid group, a phosphonic acid group, a pyrophosphoric acid group, a carboxylic acid group, and a sulfonic acid group and having at least one of an acryloyl group, a methacryloyl group, an acrylamide group, and a methacrylamide group. In view of adhesion to tooth structures, the acid group-containing (meth)acrylic polymerizable monomer (b) is preferably a monofunctional monomer having at least one of the above-mentioned acid groups and having any one of an acryloyl group, a methacryloyl group, an acrylamide group, and a methacrylamide group, as a polymerizable group. Specific examples thereof are as follows.

Examples of the phosphoric acid group-containing (meth)acrylic polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth) acryloyloxypropyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl) hydrogen phosphate, and 2-(meth)acryloyloxypropyl-(4-methoxyphenyl) hydrogen phosphate; and their acid chlorides, alkali metal salts, ammonium salts, and amine salts.

Examples of the phosphonic acid group-containing (meth)acrylic polymerizable monomer include: 2-(meth) acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth)acryloyloxydecylphosphonoacetate; and their acid chlorides, alkali metal salts, ammonium salts, and amine salts.

Examples of the pyrophosphoric acid group-containing (meth)acrylic polymerizable monomer include: bis[2-(meth) acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, and bis[10-(meth)acryloyloxydecyl] pyrophosphate; and their acid chlorides, alkali metal salts, ammonium salts, and amine salts.

Examples of the carboxylic acid group-containing (meth) acrylic polymerizable monomer include: (meth)acrylic acid, 4-[2-(meth)acryloyloxyethoxycarbonyl]phthalic acid, 4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth) acryloyloxydecyloxycarbonylphthalic acid, and their acid anhydrides; and 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth) acryloyloxy-1,1-undecanedicarboxylic acid, and their acid chlorides, alkali metal salts, ammonium salts, and amine salts.

Examples of the sulfonic acid group-containing (meth) acrylic polymerizable monomer include 2-(meth)acrylamide-2-methylpropanesulfonic acid, 2-sulfoethyl (meth)acrylate, and their acid chlorides, alkali metal salts, ammonium salts and amine salts.

Among these acid group-containing (meth)acrylic polymerizable monomers (b), the phosphoric, pyrophosphoric, or carboxylic acid group-containing (meth)acrylic polymerizable monomers are preferred since such monomers provide better bond strength to tooth structures. Particularly preferred are the phosphoric acid group-containing (meth) acrylic polymerizable monomers and the carboxylic acid group-containing (meth)acrylic polymerizable monomers. Among the phosphoric and carboxylic acid group-containing (meth)acrylic polymerizable monomers, a divalent phosphoric acid group-containing (meth)acrylic polymerizable monomer that has as the main chain of the molecule an alkyl or alkylene group having 6 to 20 carbon atoms and at least one carboxylic acid group-containing (meth)acrylic polymerizable monomer selected from the group consisting of 4-[2-(meth)acryloyloxyethoxycarbonyl]phthalic acid, 4-[2-(meth)acryloyloxyethoxycarbonyl]phthalic acid anhydride, 4-(meth)acryloyloxyethyltrimellitic acid, and 4-(meth)acryloyloxyethyltrimellitic acid anhydride are more preferable, and a divalent phosphoric acid group-containing (meth) acrylic polymerizable monomer that has as the main chain of the molecule an alkylene group having 8 to 12 carbon atoms, such as 10-methacryloyloxydecyl dihydrogen phosphate, is most preferable.

One of the above-mentioned monomers may be contained alone as the acid group-containing (meth)acrylic polymerizable monomer (b), or a combination of two or more thereof may be contained as the acid group-containing (meth)acrylic polymerizable monomer (b). The content of the acid group-containing (meth)acrylic polymerizable monomer (b) is not particularly limited as long as the effect of the present invention can be obtained. However, in order to obtain higher bond strength, the content of the acid group-containing (meth)acrylic polymerizable monomer (b) is preferably in the range of 1 to 50 parts by weight, more preferably in the range of 2 to 30 parts by weight, and most preferably in the range of 4 to 20 parts by weight in 100 parts by weight of the total polymerizable monomers.

Next, the hydrophobic crosslinkable polymerizable monomer (c) used in the present invention is described. The hydrophobic crosslinkable polymerizable monomer (c) is a hydrophobic compound having no acid group and having at least two polymerizable groups per molecule. As used herein, the term "hydrophobicity" refers to a solubility of less than 5 weight % in water at 25° C. The hydrophobic crosslinkable polymerizable monomer (c) has the effect of improving the handling properties and the mechanical strength of the dental cement of the present invention. Examples of the hydrophobic crosslinkable polymerizable monomer (c) include aromatic compound-based bifunctional polymerizable monomers, aliphatic compound-based bifunctional polymerizable monomers, and tri- or higher-functional polymerizable monomers.

Examples of the aromatic compound-based bifunctional polymerizable monomer include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane.

Examples of the aliphatic compound-based bifunctional polymerizable monomer include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylene bis(2-carbamoyloxyethyl) di(meth)acrylate, and 1,2-bis[3-methacryloxy-2-hydroxypropoxy]ethane.

Among the above-mentioned hydrophobic crosslinkable polymerizable monomers (c), aromatic compound-based bifunctional polymerizable monomers and aliphatic compound-based bifunctional polymerizable monomers are preferably used in view of the mechanical strength and handling properties. Preferable examples of the aromatic compound-based bifunctional polymerizable monomer are 2,2-bis[4-(3-(methacryloyloxy-2-hydroxypropoxy)phenyl]propane (commonly known as "Bis-GMA") and 2,2-bis(4-methacryloyloxypolyethoxyphenyl)propane (preferably having an average number of moles of added ethoxy groups of 2.6, commonly known as "D-2.6E"). Preferable examples of the aliphatic compound-based bifunctional polymerizable monomers are glycerol di(meth)acrylate, triethylene glycol di(meth)acrylate, neopentyl glycol di(meth)acrylate, 1,6-hexanediol di(meth)acrylate, 1,10-decanediol di(meth)acrylate, 1,2-bis[3-methacryloxy-2-hydroxypropoxy]ethane, and 2,2,4-trimethylhexamethylene bis(2-carbamoyloxyethyl) dimethacrylate (commonly known as "UDMA").

Among the above-mentioned hydrophobic crosslinkable polymerizable monomers (c), Bis-GMA, D-2.6E, TEGDMA, and UDMA are more preferable, and Bis-GMA, D-2.6E, and TEGDMA are even more preferable.

One of the above-mentioned monomers may be contained alone as the hydrophobic crosslinkable polymerizable monomer (c), or a combination of two or more thereof may be contained as the hydrophobic crosslinkable polymerizable monomer (c). The content of the hydrophobic crosslinkable polymerizable monomer (c) is not particularly limited as long as the effect of the present invention can be obtained. However, in order to provide not only high penetrability into a tooth structure and thus excellent bond strength but also sufficient strength to the composition, the content of the hydrophobic crosslinkable polymerizable monomer (c) is preferably in the range of 30 to 90 parts by weight, more preferably in the range of 40 to 85 parts by weight, even more preferably in the range of 50 to 80 parts by weight, and most preferably in the range of 55 to 80 parts by weight in 100 parts by weight of the total polymerizable monomers in the dental cement.

The dental cement of the present invention may further contain a hydrophilic monofuctional polymerizable monomer (f) as a polymerizable monomer component but need not necessarily contain the hydrophilic monofunctional polymerizable monomer (f). The hydrophilic monofunctional polymerizable monomer (f) refers to a monofunctional polymerizable monomer, other than the asymmetric acrylamide-methacrylic acid ester compound (a) and the acid group-containing (meth)acrylic polymerizable monomer (b), having a solubility of 5 weight % or more in water at 25° C. The hydrophilic monofunctional polymerizable monomer (f) preferably has a solubility of 10 weight % or more, and more preferably a solubility of 15 weight % or more in water at 25° C. The hydrophilic monofunctional polymerizable monomer (f) thus contained contributes to higher bond strength to dentin.

The hydrophilic monofunctional polymerizable monomer (f) has a hydrophilic group such as a hydroxyl group, an oxymethylene group, an oxyethylene group, an oxypropylene group, or an amide group. Examples of the hydrophilic monofunctional polymerizable monomer (f) include: hydrophilic monofunctional (meth)acrylate-based polymerizable monomers such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniummethyl (meth)acrylchloride; and hydrophilic monofunctional (meth)acrylamide-based polymerizable monomers such as N-methylol (meth)acrylamide, N-hydroxyethyl (meth)acrylamide, N,N-(dihydroxyethyl) (meth)acrylamide, N-methoxymethyl (meth)acrylamide, N-ethoxymethyl (meth)acrylamide, diacetone (meth)acrylamide, 4-(meth)acryloylmorpholine, N-trihydroxymethyl-N-methyl (meth)acrylamide, and a monofunctional (meth)acrylamide-based polymerizable monomer represented by the following general formula (2).

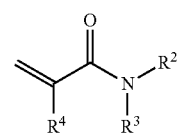

(2)

In the formula (2), $R^2$ and $R^3$ are each independently an optionally substituted, linear or branched $C_1$ to $C_3$ alkyl group, and $R^4$ is a hydrogen atom or a methyl group.

The same substituent in the formula (1) can be used as $R^2$ or $R^3$. Examples of the above-mentioned $C_1$ to $C_3$ alkyl group as $R^2$ or $R^3$ include a methyl group, an ethyl group, an n-propyl group, and an isopropyl group.

Among these hydrophilic monofunctional polymerizable monomers (f), in view of adhesion to tooth structures, 2-hydroxyethyl (meth)acrylate, 2,3-dihydroxypropyl (meth)

acrylate, diacetone (meth)acrylamide, and hydrophilic monofunctional (meth)acrylamide-based polymerizable monomers are preferable, and a monofunctional (meth) acrylamide-based polymerizable monomer represented by the general formula (2) is more preferable. One of the above-mentioned monomers may be contained alone as the hydrophilic monofunctional polymerizable monomer (f), or a combination of two or more thereof may be contained as the hydrophilic monofunctional polymerizable monomer (f).

Among the monofunctional (meth)acrylamide-based polymerizable monomers represented by the general formula (2), in view of storage stability, N,N-dimethylacrylamide and N,N-diethylacrylamide are more preferable, and N,N-diethylacrylamide is most preferable.

In the present invention, the content of the hydrophilic monofunctional polymerizable monomer (f) is not particularly limited as long as the effect of the present invention can be obtained. However, in order to obtain higher bond strength and mechanical strength, the content of the hydrophilic monofunctional polymerizable monomer (f) is preferably in the range of 1 to 30 parts by weight, more preferably in the range of 2 to 28 parts by weight, and most preferably in the range of 5 to 25 parts by weight, in 100 parts by weight of the total polymerizable monomers in the dental cement.

The dental cement of the present invention may contain a polymerizable monomer other than the above-mentioned polymerizable monomers, i.e., the asymmetric acrylamide-methacrylic acid ester compound (a), the acid group-containing (meth)acrylic polymerizable monomer (b), the hydrophobic crosslinkable polymerizable monomer (c), and the hydrophilic monofunctional polymerizable monomer (f), in order to improve its bond strength, handling properties, and mechanical strength. The dental cement of the present invention may contain, as a polymerizable monomer, a hydrophilic multifunctional (meth)acrylate-based polymerizable monomer and/or a symmetric (meth)acrylamide compound or the like to the extent that the effect of the present invention is not impaired. However, it is preferable that the dental cement contain no such polymerizable monomer or compound (be substantially free of such a polymerizable monomer or a compound). In the present description, the phrase "being substantially free of a component" means that the dental cement of the present invention contains no such component or contains only traces of the component to the extent that the effect of the dental cement of the present invention is not impaired. Examples of the hydrophilic multifunctional (meth)acrylate-based polymerizable monomer include pentaerythritol dimethacrylate, erythritol dimethacrylate, mannitol dimethacrylate, xylitol dimethacrylate, sorbitol dimethacrylate, and glycerol dimethacrylate. Examples of the symmetric (meth)acrylamide compound include compounds represented by the above formula (3) and (4) (in these formulae, what the symbols stand for is as described above). Specific examples of the symmetric (meth)acrylamide compound include bisacrylamide ethylene and N,N-diethyl-1,3-propylene-bisacrylamide.

Next, the chemical polymerization initiator (d) as a component that should be contained in the dental cement of the present invention is described. The chemical polymerization initiator (d) can be selected for use from polymerization initiators commonly used in the industrial field. Among them, chemical polymerization initiators used in dental cements are preferably used.

The chemical polymerization initiator (d) used in the present invention includes an oxidizing agent and a reducing agent.

Examples of the oxidizing agent as the chemical polymerization initiator (d) include organic peroxides, azo compounds, and inorganic peroxides. Examples of organic peroxides include diacyl peroxides, peroxyesters, dialkyl peroxides, peroxyketals, ketone peroxides, and hydroperoxides. Examples of diacyl peroxides include benzoyl peroxide, 2,4-dichlorobenzoyl peroxide, and m-toluoyl peroxide. Examples of peroxyesters include t-butyl peroxybenzoate, bis-t-butyl peroxyisophthalate, 2,5-dimethyl-2,5-bis(benzoylperoxy)hexane, t-butyl peroxy-2-ethylhexanoate, and t-butylperoxyisopropyl carbonate. Examples of dialkyl peroxides include dicumyl peroxide, di-t-butyl peroxide, and lauroyl peroxide. Examples of peroxyketals include 1,1-bis(t-butylperoxy)-3,3,5-trimethylcyclohexane, 1,1-bis(t-butylperoxy)cyclohexane, and 1,1-bis(t-hexylperoxy)cyclohexane. Examples of ketone peroxides include methyl ethyl ketone peroxide, cyclohexanone peroxide, and methyl acetoacetate peroxide. Examples of hydroperoxides include t-butyl hydroperoxide, cumene hydroperoxide, p-diisopropylbenzene hydroperoxide, and 1,1,3,3-tetramethylbutyl hydroperoxide. Examples of azo compounds include azobisisobutyronitrile and azobisisobutylvaleronitrile. Examples of inorganic peroxides include sodium persulfate, potassium persulfate, aluminum persulfate, and ammonium persulfate. One of the above-mentioned oxidizing agents may be used alone, or two or more thereof may be used in combination.

Examples of the reducing agent as the chemical polymerization initiator (d) include aromatic amines without an electron withdrawing group in the aromatic ring, thioureas, and ascorbic acid. Examples of aromatic amines without an electron withdrawing group in the aromatic ring include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. One of the above-mentioned aromatic amines without an electron withdrawing group in the aromatic ring may be used alone, or two or more thereof may be used in combination. Examples of thioureas include thiourea, methylthiourea, ethylthiourea, ethylenethiourea, N,N'-dimethylthiourea, N,N'-diethylthiourea, N,N'-di-n-propylthiourea, dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 1-(2-pyridyl)-2-thiourea, and 4,4-dimethylethylenethiourea. One of the above-mentioned thiourea compounds may be used alone, or two or more thereof may be used in combination.

Among the above-mentioned oxidizing agents and reducing agents, a combination of a hydroperoxide (as an oxidizing agent) and a thiourea (a reducing agent) and a combination of a diacyl peroxide and/or an inorganic peroxide (as an oxidizing agent) and an aromatic amine without an electron withdrawing group in the aromatic ring (as a reducing agent) are preferably used in view of the curability of the resulting composition.

The total content of an oxidizing agent and a reducing agent as the chemical polymerization initiator (d) is not particularly limited. In view of the mechanical strength and the bond strength of the resulting dental cement, the total content of the chemical polymerization initiators (d) is preferably 0.01 to 20 parts by weight, more preferably 0.05 to 10 parts by weight, and most preferably 0.1 to 5 parts by weight, with respect to 100 parts by weight of the total polymerizable monomers.

The dental cement of the present invention contains the above-mentioned chemical polymerization type polymerization initiator system. The dental cement of the present invention may further contain a conventionally known photopolymerization initiator as a component other than the above-mentioned chemical polymerization initiator (d) so as to form a dual cure type composition whose polymerization is initiated upon irradiation with light. Examples of the photopolymerization initiator include photopolymerization initiators that may be used in dental cements such as (bis)acylphosphine oxides, water-soluble acylphosphine oxides, thioxanthones, quaternary ammonium salts of thioxanthones, ketals, α-diketones, coumarins, anthraquinones, benzoin alkyl ether compounds, and α-aminoketone compounds. Among these photopolymerization initiators, at least one selected from the group consisting of (bis)acylphosphine oxides and α-diketones is preferably used. Among these (bis)acylphosphine oxides, 2,4,6-trimethylbenzoyldiphenylphosphine oxide is particularly preferably used, and among these α-diketones, camphorquinone is particularly preferably used.

The content of the photopolymerization initiator is not particularly limited. In view of the curability of the resulting dental cement, the content of the photopolymerization initiator is preferably 0.01 to 10 parts by weight, more preferably 0.05 to 5 parts by weight, and most preferably 0.1 to 3 parts by weight, with respect to 100 parts by weight of the total polymerizable monomers.

In a preferred embodiment of the present invention, the above-mentioned chemical polymerization initiator (d) and/or photopolymerization initiator is used in combination with a polymerization accelerator (g). Examples of the polymerization accelerator (g) that may be used in the present invention include aliphatic amines, aromatic tertiary amines having an electron withdrawing group, sulfinic acids, sulfinates, sulfur-containing reducing inorganic compounds, borate compounds, barbituric acid derivatives, triazine compounds, copper compounds, tin compounds, vanadium compounds, halogen compounds, aldehydes, and thiol compounds.

Examples of the aliphatic amine include: primary aliphatic amines such as n-butylamine, n-hexylamine, and n-octylamine; secondary aliphatic amines such as diisopropylamine, dibutylamine, and N-methylethanolamine; tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine mono(meth)acrylate, triethanolamine di(meth)acrylate, triethanolamine tri(meth)acrylate, triethanolamine, trimethylamine, triethylamine, and tributylamine. Among these, tertiary aliphatic amines are preferably used in view of the curability and storage stability of the composition, and in particular, N-methyldiethanolamine and triethanolamine are preferably used.

Examples of the aromatic tertiary amine having an electron withdrawing group include compounds in which a hydrogen atom of the aromatic ring of the aromatic tertiary amine is substituted by an electron withdrawing group such as a carboxyl group, a carboxylic ester group, a nitrile group, a halogen group, or the like. Specific examples of such a compound include ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, and 4-(N,N-dimethylamino)benzophenone. Among these, ethyl 4-(N,N-dimethylamino)benzoate, methyl 4-(N,N-dimethylamino)benzoate, n-butoxyethyl 4-(N,N-dimethylamino)benzoate, and 4-(N,N-dimethylamino)benzophenone are preferable in view of the curability of the resulting composition.

Examples of the sulfinic acids and sulfinates include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate.

Examples of the sulfur-containing reducing inorganic compound include sulfites, bisulfites, pyrosulfites, thiosulfates, thionates, and dithionites. Specific examples thereof include sodium sulfite, potassium sulfite, calcium sulfite, ammonium sulfite, sodium bisulfite, and potassium bisulfite.

The borate compound is preferably an aryl borate compound. Specific examples of aryl borate compounds that are suitable for use as the polymerization accelerator include borate compounds having one aryl group per molecule, such as trialkylphenylboron, trialkyl(p-chlorophenyl)boron, trialkyl(p-fluorophenyl)boron, trialkyl[(3,5-bistrifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (their alkyl groups are each at least one selected from the group consisting of, for example, an n-butyl group, an n-octyl group, and an n-dodecyl group), and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound include those that have two aryl groups per molecule, such as dialkyldiphenylboron, dialkyldi(p-chlorophenyl)boron, dialkyldi(p-fluorophenyl)boron, dialkyl[di(3,5-bis-trifluoromethyl)phenyl]boron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (their alkyl groups are each at least one selected from the group consisting of, for example, an n-butyl group, an n-octyl group, and an n-dodecyl group), and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound further include those that have three aryl groups per molecule, such as monoalkyltriphenylboron, monoalkyltri(p-chlorophenyl)boron, monoalkyltri(p-fluorophenyl)boron, monoalkyltri(3,5-bis-trifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl)boron (their alkyl groups are each at least one selected from, for example, an n-butyl group, an n-octyl group, and an n-dodecyl group), and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compound further include those that have four aryl groups per molecule, such as tetraphenylboron, tetrakis(p-chlorophenyl)boron, tetrakis(p-fluorophenyl)boron, tetrakis[(3,5-bistrifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [(3,5-bistrifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron, and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the barbituric acid derivatives include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cydohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cydohexylbarbituric acid, 1-benzyl-5-phenylbarbituric acid, and thiobarbituric acids; and salts of the barbituric acids (alkali metal salts and alkaline earth metal salts are particularly preferable). Examples of the salts of the barbituric acids include sodium 5-butylbarbiturate, sodium 1,3,5-trimethylbarbiturate, and sodium 1-cyclohexyl-5-ethylbarbiturate.

Examples of the triazine compounds include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Preferable examples of the copper compounds include copper acetylacetonate, copper (II) acetate, copper oleate, copper (II) chloride, and copper (II) bromide.

Examples of the tin compounds include di-n-butyltin dimaleate, di-n-octyltin dimaleate, di-n-octyltin dilaurate, and di-n-butyltin dilaurate. Particularly preferred tin compounds are di-n-octyltin dilaurate and di-n-butyltin dilaurate.

The vanadium compound is preferably a compound of tetravalent and/or pentavalent vanadium. Examples of the compound of tetravalent and/or pentavalent vanadium include compounds mentioned in JP 2003-96122 A, such as divanadium (IV) tetroxide, vanadium (IV) oxide acetylacetonate, vanadyl (IV) oxalate, vanadyl (IV) sulfate, oxobis(1-phenyl-1,3-butanedionato)vanadium (IV), bis(maltolato)oxovanadium (IV), vanadium (V) pentoxide, sodium metavanadate (V), and ammonium metavanadate (V).

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde.

Examples of the thiol compounds include 3-mercaptopropyltrimethoxysilane, 2-mercaptobenzoxazole, decanethiol, and thiobenzoic acid.

Among the above-mentioned polymerization accelerators (g), preferred are tertiary aliphatic amines, sulfinic acids, sulfinates, sulfur-containing reducing inorganic compounds, copper compounds, and vanadium compounds. Among them, more preferred is at least one selected from the group consisting of: tertiary aliphatic amines such as N-methyldiethanolamine and triethanolamine; sulfinic acids and sulfinates such as sodium p-toluenesulfinate, sodium benzenesulfinate, and sodium 2,4,6-triisopropylbenzenesulfinate; sulfur-containing reducing inorganic compounds such as sodium sulfite, potassium sulfite, calcium sulfite, ammonium sulfite, sodium bisulfite, and potassium bisulfite; copper compounds such as copper acetylacetonate and copper (II) acetate; and vanadium compounds such as vanadium (IV) oxide acetylacetonate and bis(maltolato)oxovanadium (IV). When the dental cement of the present invention contains a photopolymerization initiator, an aromatic tertiary amine having an electron withdrawing group, such as N,N-di(2-hydroxyethyl)-p-toluidine, ethyl 4-(N,N-dimethylamino)benzoate, n-butoxyethyl 4-(N,N-dimethylamino)benzoate, 4-(N,N-dimethylamino)benzophenone, or the like is preferably used as a polymerization accelerator (g).

One of the above-mentioned polymerization accelerators (g) may be used alone, or two or more thereof may be used in combination. The content of the polymerization accelerator (g) is not particularly limited. In view of the curability, etc. of the resulting composition, the content of the polymerization accelerator (g) is preferably 0.01 to 20 parts by weight, more preferably 0.05 to 10 parts by weight, and most preferably 0.1 to 5 parts by weight, with respect to 100 parts by weight of the total polymerizable monomers.

The filler (e) as a component that should be contained in the dental cement of the present invention is described. The fillers (e) that may be used in the dental cement of the present invention are classified broadly into organic fillers, inorganic fillers, and organic-inorganic composite fillers.

Examples of the material of the organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or a mixture of two or more thereof may be used. The shape of the organic filler is not particularly limited, and the particle diameter of the filler used can be selected as appropriate. In view of the characteristics such as handling properties and mechanical strength of the resulting dental cement, the average particle diameter of the organic filler is preferably 0.001 to 50 μm and more preferably 0.001 to 10 μm. The organic filler may be a combination of ultrafine particles having an average particle diameter of 0.001 to 0.1 μm and macro-particles having an average particle diameter of 1 to 50 μm (preferably 1 to 10 μm). In the present description, the average particle diameter of the filler means the average particle diameter of the primary particles of the filler (i.e., the average primary particle diameter).

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. When at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass is used, among the above-mentioned inorganic filler materials, it is possible to provide fluorine sustained releasability to the dental cement of the present invention. On the other hand, when at least one selected from the group consisting of barium glass, strontium glass, barium boroaluminosilicate glass, strontium boroaluminosilicate glass, strontium fluoroaluminosilicate glass, and barium fluoroaluminosilicate glass is used, among the above-mentioned inorganic filler materials, it is possible to provide high radiopacity to the dental cement of the present invention. These inorganic fillers may be used alone or a mixture of two or more thereof may be used. The shape of the inorganic filler is not particularly limited, and the particle diameter of the filler used can be selected as appropriate. In view of the characteristics such as handling properties and mechanical strength of the resulting dental cement, the average particle diameter of the inorganic filler is preferably 0.001 to 50 μm and more preferably 0.001 to 10 μm. The inorganic filler may be a combination of ultrafine particles having an average particle diameter of 0.001 to 0.1 μm and macro-particles having an average particle diameter of 1 to 50 μm (preferably 1 to 10 μm).

Examples of the shape of the inorganic filler include an irregular shape and a spherical shape. The shape of the inorganic filler to be used in the dental cement of the present invention can be selected as appropriate in view of the characteristics such as handling properties and mechanical strength of the resulting dental cement.

The inorganic filler may be surface-treated beforehand with a commonly-known surface treatment agent such as a silane coupling agent where necessary in order to adjust the flowability of the dental cement. Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler is obtainable by adding a monomer compound to the above inorganic filler, forming the mixture into a paste, then subjecting the paste to polymerization, and grinding the resulting polymerization product. The organic-inorganic composite filler used can be, for example, a TMPT filler (obtainable by mixing trimethylolpropane methacrylate and a silica filler, subjecting the mixture to polymerization, and then grinding the resulting polymerization product). The shape of the organic-inorganic composite filler is not particularly limited, and the particle diameter of the filler used can be selected as appropriate. In view of the characteristics such as handling properties and mechanical strength of the resulting dental cement, the average particle diameter of the organic-inorganic composite filler is preferably 0.001 to 50 μm and more preferably 0.001 to 10 μm. The organic-inorganic composite filler may be a combination of ultrafine particles having an average particle diameter of 0.001 to 0.1 μm and macro-particles having an average particle diameter of 1 to 50 μm (preferably 1 to 10 μm).

Among the above-mentioned fillers (e), inorganic fillers are preferably used in view of the handling properties and mechanical strength of the resulting dental cement. At least one selected from the group consisting of quartz, silica, alumina, silica-zirconia, lanthanum glass, barium glass, strontium glass, fluoroaluminosilicate glass, and barium fluoroaluminosilicate glass is more preferably used. In the present invention, a commercially available filler may be used as the filler (e).

In the present description, the average particle diameter of the filler can be determined by the laser diffraction scattering method or by electron microscopic observation of the particles. Specifically, the laser diffraction scattering method is convenient for particle diameter measurement of particles with a diameter of 0.1 µm or more, and the electron microscopic observation is convenient for particle diameter measurement of ultrafine particles with a diameter of 0.1 µm or less. 0.1 µm is the value measured by the laser diffraction scattering method.

To be more specific about the laser diffraction scattering method, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about the electron microscopic observation, for example, the average particle diameter can be measured by taking a photograph of the particles with a scanning electron microscope (S-4000, manufactured by Hitachi, Ltd.) and measuring the particle diameters of (200 or more) particles observed in a unit area of field of view in the photograph by the use of an image-analyzing particle size distribution analysis software (MacView manufactured by Mountech Co., Ltd.). In this case, the particle diameter of each particle is obtained as an arithmetic mean value of the longest and shortest dimensions thereof, and the average primary particle diameter is calculated from the number of the particles and their particle diameters.

In the present invention, two or more fillers having different materials, particle size distributions, and forms may be mixed or combined for use. Particles other than the filler particles may be unintentionally contained as impurities, as long as the effect of the present invention is not impaired.

The content of the filler (e) used in the present invention is not particularly limited as long as the effect of the present invention can be obtained. In order to obtain a cured product having sufficient mechanical strength and a dental cement having excellent handling properties, the content of the filler (e) is preferably in the range of 40 to 900 parts by weight, more preferably in the range of 100 to 500 parts by weight, and even most preferably in the range of 150 to 400 parts by weight, with respect to 100 parts by weight of the total polymerizable monomers.

Furthermore, the dental cement of the present invention may contain, for example, water, an organic solvent, a pH adjuster, a polymerization inhibitor, an ultraviolet absorber, a thickener, a colorant, an antibacterial agent, or a flavor as long as the effect of the present invention is not impaired.

A preferred embodiment of the dental cement of the present invention is, for example, a dental cement containing 2 to 50 parts by weight of the asymmetric acrylamide-methacrylic acid ester compound (a), 1 to 50 parts by weight of the acid group-containing (meth)acrylic polymerizable monomer (b), 30 to 90 parts by weight of the hydrophobic crosslinkable polymerizable monomer (c), and 1 to 30 parts by weight of the hydrophilic monofunctional polymerizable monomer (f) as an optional component in 100 parts by weight of the total polymerizable monomers, and further containing 0.01 to 20 parts by weight of the chemical polymerization initiator (d), 0.01 to 10 parts by weight of the photopolymerization initiator, 0.01 to 20 parts by weight of the polymerization accelerator (g), and 40 to 900 parts by weight of the filler (e) with respect to 100 parts by weight of the total polymerizable monomers.

A more preferred embodiment of the dental cement of the present invention is, for example, a dental cement containing 5 to 40 parts by weight of the asymmetric acrylamide-methacrylic acid ester compound (a), 2 to 30 parts by weight of the acid group-containing (meth)acrylic polymerizable monomer (b), 40 to 85 parts by weight of the hydrophobic crosslinkable polymerizable monomer (c), and 2 to 28 parts by weight of the hydrophilic monofunctional polymerizable monomer (f) as an optional component in 100 parts by weight of the total polymerizable monomers, and further containing 0.05 to 10 parts by weight of the chemical polymerization initiator (d), 0.05 to 5 parts by weight of the photopolymerization initiator, 0.05 to 10 parts by weight of the polymerization accelerator (g), and 100 to 500 parts by weight of the filler (e) with respect to 100 parts by weight of the total polymerizable monomers.

An even more preferred embodiment of the dental cement of the present invention is, for example, a dental cement containing 10 to 30 parts by weight of the asymmetric acrylamide-methacrylic acid ester compound (a), 4 to 20 parts by weight of the acid group-containing (meth)acrylic polymerizable monomer (b), 50 to 80 parts by weight of the hydrophobic crosslinkable polymerizable monomer (c), and 5 to 25 parts by weight of the hydrophilic monofunctional polymerizable monomer (f) as an optional component in 100 parts by weight of the total polymerizable monomers, and further containing 0.1 to 5 parts by weight of the chemical polymerization initiator (d), 0.1 to 3 parts by weight of the photopolymerization initiator, 0.1 to 3 parts by weight of the polymerization accelerator (g), and 150 to 400 parts by weight of the filler (e) with respect to 100 parts by weight of the total polymerizable monomers.

The dental cement of the present invention can be prepared in a conventional manner depending on the above-mentioned components contained therein. In view of the storage stability, the dental cement of the present invention is divided into a first group of components including an oxidizing agent as a chemical polymerization initiator (d) and a second group of components including a reducing agent as a chemical polymerization initiator (d), which are stored in separate containers. That is, the dental cement of the present invention is used in the form of a two-part (multi-part) cement. For example, the form of the dental cement can be selected as appropriate from various two-part forms such as a powder-liquid form, a paste-liquid form, and a paste-paste form (two-paste form). In view of the handling properties, the dental cement is used in the two-paste form in a more preferred embodiment. Preferably, these two pastes are stored separately from each other and mixed to form a mixture immediately before use so as to allow chemical polymerization to proceed and to achieve curing of the mixture. Usually, the two pastes are each prepared by mixing a filler (e) (powder) and a liquid component prepared by mixing the components other than the filler (e).

As described above, the dental cement of the present invention is used in the form of a two-part cement containing a first part and a second part. The combination of the first part and the second part is not particularly limited as long as the first part contains a chemical polymerization initiator serving as an oxidizing agent and the second part contains a chemical polymerization initiator serving as a reducing agent. In view of the storage stability, it is preferable that the first part contain both the acid group-containing (meth)acrylic polymerizable monomer (b) and the chemical polymerization initiator (d) serving as an oxidizing agent. Specific examples of the preferable combination of the two parts in the dental cement of the present invention include:

1) a combination of a first part containing an asymmetric acrylamide-methacrylic acid ester compound (a), an acid group-containing (meth)acrylic polymerizable monomer (b), a hydrophobic crosslinkable polymerizable monomer (c), a hydrophilic monofunctional polymerizable monomer (f), a chemical polymerization initiator (d) serving as an oxidizing agent, and a filler (e) and a second part containing an asymmetric acrylamide-methacrylic acid ester compound (a), a hydrophobic crosslinkable polymerizable monomer (c), a chemical polymerization initiator (d) serving as a reducing agent, and a filler (e); and 2) a combination of a first part containing an asymmetric acrylamide-methacrylic acid ester compound (a), an acid group-containing (meth)acrylic polymerizable monomer (b), a hydrophobic crosslinkable polymerizable monomer (c), a chemical polymerization initiator (d) serving as an oxidizing agent, and a filler (e) and a second part containing an asymmetric acrylamide-methacrylic acid ester compound (a), a hydrophobic crosslinkable polymerizable monomer (c), a chemical polymerization initiator (d) serving as a reducing agent, and a filler (e).

When the dental cement of the present invention contains a polymerization accelerator (g), it is preferable that the polymerization accelerator (g) and a chemical polymerization initiator (d) serving as a reducing agent be contained in the same part. Preferably, the dental cement of the present invention is a non-aqueous system. For example, the non-aqueous dental cement is a two-part (multi-part) type cement, in which one of the first part and the second part may be a non-aqueous system, but preferably, both the first part and the second part contain no water.

When the dental cement of the present invention is used for luting dental prostheses such as crowns, inlays, and bridges to broken or chipped portions of affected teeth, luting with high bond strength can be achieved. In order to further enhance the adhesion, the dental cement of the present invention may be used in combination with a self-etching primer or a dental adhesive.

The present invention encompasses embodiments obtainable by combining the above embodiments in various manners within the technical scope of the present invention as long as the effect of the present invention can be obtained.

EXAMPLES

Hereinafter, the present invention will be described in more detail by way of examples. It should be noted that the present invention is not limited by any means by the following examples and many modifications can be made by those having ordinary skill in the art within the technical scope of the present invention. Abbreviations used hereinafter are as follows.

[Asymmetric Acrylamide-Methacrylic Acid Ester Compound (a)]

MAEA: N-methacryloyloxyethyl acrylamide (asymmetric acrylamide-methacrylic acid ester compound represented by the following formula):

MAPA: N-methacryloyloxypropyl acrylamide (asymmetric acrylamide-methacrylic acid ester compound represented by the following formula):

MAEEA: N-(1-ethyl-(2-methacryloyloxy)ethyl) acrylamide (asymmetric acrylamide-methacrylic acid ester compound represented by the following formula):

MAEGA: N-(2-(2-methacryloyloxyethoxy)ethyl) acrylamide (asymmetric acrylamide-methacrylic acid ester compound represented by the following formula):

Hydrophilic multifunctional (meth)acrylate-based polymerizable monomer
ErMA: Pentaerythritol dimethacrylate
EDMA: Erythritol dimethacrylate[1,4-bis(methacryloyloxy)-2,3-butanediol]
Symmetric (meth)acrylamide-based polymerizable monomer
BAAE: Bisacrylamide ethylene
DEPBAA: N,N-diethyl-1,3-propylene-bisacrylamide
[Acid Group-Containing (Meth)Acrylic Polymerizable Monomer (b)]
MDP: 10-methacryloyloxydecyl dihydrogen phosphate
4-META: 4-[2-(methacryloyloxy)ethoxycarbonyl] phthalic acid anhydride
[Hydrophobic Crosslinkable Polymerizable Monomer (c)]
Bis-GMA: 2,2-bis[4-(3-methacryloyloxy-2-hydroxypropoxy)phenyl]propane
D-2.6E: 2,2-bis(4-methacryloyloxypolyethoxyphenyl) propane (having an average number of moles of added ethoxy groups of 2.6)
TEGDMA: Triethylene glycol dimethacrylate
[Hydrophilic Monofunctional Polymerizable Monomer (f)]
Hydrophilic monofunctional (meth)acrylamide-based polymerizable monomer
DEAA: N,N-diethylacrylamide
DMAA: N,N-dimethylacrylamide
Hydrophilic monofunctional (meth)acrylate-based polymerizable monomer
HEMA: 2-hydroxyethyl methacrylate
Photopolymerization Initiator
CQ: dl-camphorquinone
[Chemical Polymerization Initiator (d)]
Chemical polymerization initiator (Oxidizing agent)
THP: 1,1,3,3-tetramethylbutyl hydroperoxide
BPO: benzoyl peroxide Chemical polymerization initiator (Reducing agent)
PTU: 1-(2-pyridyl)-2-thiourea
DEPT: N,N-di(2-hydroxyethyl)-p-toluidine
[Polymerization Accelerator (g)]
DABE: Ethyl 4-(N,N-dimethylamino)benzoate
TPBSS: Sodium 2,4,6-trilsopropylbenzenesulfinate
[Filler (e)]
Inorganic Filler 1: Silane-Treated Barium Glass Powder Barium glass (manufactured by Esstech, Inc., Product code "E-3000") was ground in a ball mill to obtain a barium glass powder. The average particle diameter of the barium glass powder thus obtained was measured using a laser diffraction particle size distribution analyzer (manufactured by Shimadzu Corporation, Model "SALD-2100"). As a result, the average particle diameter was 2.4 μm. 100 parts by weight of this barium glass powder was surface-treated with 3 parts by weight of γ-methacryloxypropyltrimethoxysilane. Thus, a silane-treated barium glass powder was obtained.

Inorganic Filler 2: Silane-Treated Colloidal Silica Powder 0.3 parts by weight of acetic acid and 3 parts by weight of γ-methacryloxypropyltrimethoxysilane were added to 100 parts by weight of distilled water and the resulting mixture was stirred. Then, 50 parts by weight of colloidal silica powder (manufactured by Nippon Aerosil Co., Ltd., Product code "Aerosil OX 50" having an average particle diameter of 40 nm) was further added and the resulting mixture was stirred for 1 hour. Water was removed from the resulting solution by lyophilization, followed by heat treatment at 80° C. for 5 hours. Thus, a silane-treated colloidal silica powder was obtained.

Others

BHT: 2,6-di-t-butyl-4-methylphenol (stabilizer (polymerization inhibitor))

(Synthesis Example 1) Synthesis of MAEA 172.7 g (1.5 mol) of hydroxyethyl acrylamide (manufactured by Kohjin Film & Chemicals Co., Ltd.), 167 g (1.65 mol) of triethylamine, 38 mg (0.3 mmol) of p-methoxyphenol, and 1500 mL of anhydrous tetrahydrofuran were put into a 10-liter four-necked flask, stirred, and cooled to an internal temperature of −10° C. 700 mL of an anhydrous tetrahydrofuran solution of methacrylic acid chloride (172.5 g, 1.65 mol) was added dropwise at 5° C. or lower over 2 hours. After the dropwise addition of the solution, the resulting mixture was stirred for 24 hours under the conditions of room temperature. The resulting reaction solution was filtered, and insoluble matters were washed with ethyl acetate. The filtrate was concentrated under reduced pressure, and the residue was dissolved in ethyl acetate. The resulting solution was filtered with Celite to remove a small amount of insoluble matters, and then the filtrate was washed with a mixture of saturated saline solution and purified water (1:1). The organic layer was dried with anhydrous sodium sulfate, and then concentrated at 35° C. or lower under reduced pressure. The concentrated residue thus obtained was purified by silica gel column chromatography (developing solvent: ethyl acetate). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 201.2 g, and the percentage yield was 73.3%.

MS m/z: 184 (M+H)$^+$ $^1$H-NMR (270 MHz CDCl$_3$): δ 1.94 (m, 3H), 3.62 (m, 2H), 4.28 (m, 2H), 5.58 (m, 1H), 5.66 (m, 1H), 6.08 (s, 1H), 6.10 (m, 1H), 6.11 (m, 1H), 6.28 (m, 1H) (ppm)

(Synthesis Example 2) Synthesis of MAPA 23.9 g (0.318 mol) of 3-aminopropanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

12.9 g (0.1 mol) of hydroxypropyl acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent: ethyl acetate/hexane=2/1). After the column purification, the solvent was removed under reduced pressure using a rotary evaporator. Thus, a white solid was obtained. The solid was subjected to LC-MS analysis and $^1$H-NMR measurement. It was determined from the locations and integrals of signals that the white solid thus obtained was a target compound. The weight yield was 11.1 g, and the percentage yield was 56.3%.

MS m/z: 198 (M+H)$^+$ $^1$H-NMR (270 MHz CDCl$_3$): δ 1.93 (m, 2H), 1.97 (m, 3H), 3.42 (m, 2H), 4.27 (m, 2H), 5.58 (m, 1H), 5.65 (m, 1H), 6.11 (s, 1H), 6.10 (m, 1H), 6.13 (m, 1H), 6.30 (m, 1H) (ppm)

(Synthesis Example 3) Synthesis of MAEEA 28.3 g (0.318 mol) of DL-2-amino-1-butanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

14.3 g (0.1 mol) of N-(1-ethyl-(2-hydroxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent: ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 7.7 g, and the percentage yield was 36.3%.

MS m/z: 212 (M+H)$^+$ $^1$H-NMR (270 MHz DMSO-d$_6$): δ 0.81 (m, 3H), 1.44 (m, 2H), 1.94 (m, 3H), 3.75 (m, 1H), 4.42 (m, 2H), 5.57 (m, 1H), 5.65 (m, 1H), 6.11 (m, 1H), 6.13 (m, 1H), 6.28 (m, 1H), 8.04 (s, 1H) (ppm)

(Synthesis Example 4) Synthesis of MAEGA 33.4 g (0.318 mol) of 2-(2-aminoethoxy)ethanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

15.9 g (0.1 mol) of N-(2-(2-hydroxyethoxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent: ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 10.4 g, and the percentage yield was 45.8%.

MS m/z: 228 (M+H)$^+$ $^1$H-NMR (270 MHz DMSO-d$_6$): δ 1.93 (m, 3H), 3.28 (m, 2H), 3.43 (m, 2H), 3.49 (m, 2H), 4.34 (m, 2H), 5.59 (m, 1H), 5.63 (m, 1H), 6.09 (m, 1H), 6.12 (m, 1H), 6.30 (m, 1H), 8.17 (s, 1H) (ppm)

BAAE

N,N'-ethylenebisacrylamide (manufactured by Alfa Aesar) was used.

DEPBAA

N,N-diethyl-1,3-propylene-bisacrylamide was synthesized according to the method disclosed in Example 2 of JP 2002-212019 A. Specifically, 36.3 g (0.40 mol) of acrylic acid chloride and 4 mg of monomethyl ether hydroquinone (MEHQ) were dissolved in 1.2 L of acetonitrile in a 2.5-liter sulfonation flask and cooled to −5° C. Next, 1.2 L of an acetonitrile solution of N,N'-diethylpropylene diamine (46.9 g, 0.36 mol) was added dropwise with stirring to keep the temperature between −5° C. and 0° C. 1.5 hours later, the temperature of the resulting mixture was raised to room temperature and then stirred for 4 hours. Next, the formed precipitate was filtered and washed with 0.5 L of acetonitrile. The acetonitrile phases were combined and concentrated under reduced pressure (10 mbar, 40° C.). The crude product was dissolved in 150 mL of acetone, filtered through a frit containing 50 g of silica gel 60, and then concentrated again. This process was repeated. As a result, 32.7 g (a percentage yield of 76%) of a pale yellow liquid (η(23° C.)=270 mPa·s) was obtained.

Examples 1 to 10

The materials prepared in the above-mentioned synthesis examples were used to prepare two-paste type dental cements having the compositions shown in Table 1. The dental cements were specifically described below. All the components shown in Table 1 except for the filler (e) (powder) were mixed at ordinary temperature, and the mixed states of the resulting liquid components were tested by the following method. Subsequently, the homogeneous liquid components thus obtained were each mixed with the filler (e) (powder) to prepare a paste A and a paste B. Next, these pastes were mixed at a mass ratio of 1:1 to prepare a dental cement, and then the tensile bond strength to dentin and the flexural strength of the resulting cured product were measured by the following procedures. Table 1 shows the content (parts by weight) of each component of this dental cement and the test results thereof.

[Mixed State Test Method for Liquid Component of Dental Cement]

When each paste for a dental cement was prepared, a liquid component prepared by mixing all the components other than the filler (e) (powder) at ordinary temperature was placed in a glass bottle and visually observed from outside the bottle to determine whether the liquid component was cloudy or even partially phase-separated so as to evaluate the mixed state. The cloudy or even partially phase-separated liquid components were determined to be "inhomogeneous" and the liquid components with no cloudiness nor phase separation were determined to be "homogeneous", and the former was rated "poor" and the latter was rated "good".

[Measurement of Tensile Bond Strength to Dentin]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined. The cement composition obtained by mixing the above-mentioned paste A and paste B was applied to one end face (circular end face) of a cylindrical stainless steel rod (with a diameter of 7 mm and a length of 2.5 cm). The cylindrical stainless steel rod was placed on the circular hole of the adhesive tape so that the center of the cylindrical stainless steel rod coincided with the center of the circular hole, and then the end face to which the cement composition was applied was pressed against the adhesive tape. Thus, the cylindrical stainless steel rod was planted perpendicularly to the dentin surface. Thereafter, an excess of the cement composition flowing from around the stainless steel cylindrical rod was removed with an instrument, and the resulting sample was allowed to stand at room temperature for 30 minutes and then immersed in distilled water. Five test samples were prepared in total for the bond strength test. All the test samples immersed in distilled water were allowed to stand in a thermostat set at 37° C. for 24 hours. Then, the tensile bond test was carried out using a universal testing machine (manufactured by Shimadzu Corporation) with a crosshead speed set at 2 mm/minute. The average of the measured values of these five test samples was employed as the value of the tensile bond strength to dentin of the composition of each example.

[Measurement of Flexural Strength of Cured Product]

A polyester film was placed over a glass slide and a stainless steel mold of 2 mm long, 25 mm wide, and 2 mm deep was placed on the film. Next, a composition obtained by mixing the paste A and the paste B at a mass ratio of 1:1 was poured into the mold. A polyester film was placed on the composition in the mold and then a glass slide was placed on the polyester film, so that the composition in the mold was sandwiched between the two glass slides, which were clamped with a 25-mm wide alligator clip. The sample clamped with the alligator clip was allowed to stand in a thermostat at 37° C. for 1 hour to cure through polymerization. Then, the sample was removed from the thermostat, and the polymerized cured product of the composition was removed from the mold. The polymerized cured product was immersed in distilled water at 37° C. for 24 hours for storage, and the resulting product was used as a test sample and subjected to a bending test. The test sample was subjected to a three-point bending test using a universal testing machine (manufactured by Shimadzu Corporation) with a span of 20 mm and a crosshead speed of 1 mm/min so as to measure the flexural strength of the test sample. The average of the measured values of five test samples was employed as the value of the flexural strength of the cured product of each example.

TABLE 1

| | | Ex. 1 | | Ex. 2 | | Ex. 3 | | Ex. 4 | | Ex. 5 | |
|---|---|---|---|---|---|---|---|---|---|---|---|
| | | A | B | A | B | A | B | A | B | A | B |
| Asymmetric acrylamide-methacrylic acid ester compound (a) | MAEA | 20 | 20 | — | — | — | — | — | — | 25 | 20 |
| | MAPA | — | — | 20 | 20 | — | — | — | — | — | — |
| | MAEEA | — | — | — | — | 20 | 20 | — | — | — | — |
| | MAEGA | — | — | — | — | — | — | 20 | 20 | — | — |
| Acid group-containing (meth)acrylic polymerizable monomer (b) | MDP | 10 | — | 10 | — | 10 | — | 10 | — | — | — |
| | 4-META | — | — | — | — | — | — | — | — | 5 | — |
| Hydrophobic crosslinkable polymerizable monomer (c) | Bis-GMA | 20 | 20 | 20 | 20 | 20 | 20 | 20 | 20 | 20 | 20 |
| | D-2.6E | 25 | 35 | 25 | 35 | 25 | 35 | 25 | 35 | 25 | 35 |
| | TEGDMA | 25 | 25 | 25 | 25 | 25 | 25 | 25 | 25 | 25 | 25 |
| Hydrophilic monofunctional (meth)acrylamide-based polymerizable monomer (f) | DEAA | — | — | — | — | — | — | — | — | — | — |
| | DMAA | — | — | — | — | — | — | — | — | — | — |
| Hydrophilic monofunctional (meth)acrylate-based polymerizable monomer (f) | HEMA | — | — | — | — | — | — | — | — | — | — |
| Photopolymerization initiator | CQ | 0.3 | — | 0.3 | — | 0.3 | — | 0.3 | — | 0.3 | — |
| Chemical polymerization initiator (oxidizing agent) (d) | THP | 3 | — | 3 | — | 3 | — | 3 | — | 3 | — |
| | BPO | — | — | — | — | — | — | — | — | — | — |
| Chemical polymerization initiator (reducing agent) (d) | PTU | — | 1 | — | 1 | — | 1 | — | 1 | — | 1 |
| | DEPT | — | — | — | — | — | — | — | — | — | — |
| Polymerization accelerator (g) | DABE | — | 0.4 | — | 0.4 | — | 0.4 | — | 0.4 | — | 0.4 |
| | TPBSS | — | — | — | — | — | — | — | — | — | — |
| Polymerization inhibitor | BHT | 0.1 | 0.1 | 0.1 | 0.1 | 0.1 | 0.1 | 0.1 | 0.1 | 0.1 | 0.1 |
| Filler (e) | Inorganic filler 1 | 140 | 140 | 140 | 140 | 140 | 140 | 140 | 140 | 140 | 140 |
| | Inorganic filler 2 | 45 | 45 | 45 | 45 | 45 | 45 | 45 | 45 | 45 | 45 |
| Mixed state of liquid component | | good | good | good | good | good | good | good | good | good | good |
| Tensile bond strength to dentin (unit: MPa) | | 8.3 | | 7.2 | | 6.4 | | 6.1 | | 5.8 | |
| Flexural strength of cured product (unit: MPa) | | 124 | | 127 | | 123 | | 118 | | 128 | |

| | | Ex. 6 | | Ex. 7 | | Ex. 8 | | Ex. 9 | | Ex. 10 | |
|---|---|---|---|---|---|---|---|---|---|---|---|
| | | A | B | A | B | A | B | A | B | A | B |
| Asymmetric acrylamide-methacrylic acid ester compound (a) | MAEA | 20 | 20 | 20 | 20 | 20 | 20 | 20 | 20 | 20 | 20 |
| | MAPA | — | — | — | — | — | — | — | — | — | — |
| | MAEEA | — | — | — | — | — | — | — | — | — | — |
| | MAEGA | — | — | — | — | — | — | — | — | — | — |

TABLE 1-continued

| | | | | | | | | | | | |
|---|---|---|---|---|---|---|---|---|---|---|---|
| Acid group-containing (meth)acrylic polymerizable monomer (b) | MDP | 10 | — | 10 | — | 10 | — | 10 | — | 10 | — |
| | 4-META | — | — | — | — | — | — | — | — | — | — |
| Hydrophobic crosslinkable polymerizable monomer (c) | Bis-GMA | 20 | 20 | 20 | 20 | 20 | 20 | 20 | 20 | 20 | 20 |
| | D-2.6E | 25 | 35 | 25 | 35 | 25 | 35 | 25 | 35 | 25 | 35 |
| | TEGDMA | 25 | 25 | — | 25 | — | 25 | — | 25 | — | — |
| Hydrophilic monofunctional (meth)acrylamide-based polymerizable monomer (f) | DEAA | — | — | 25 | — | — | — | — | — | — | — |
| | DMAA | — | — | — | — | 25 | — | — | — | — | — |
| Hydrophilic monofunctional (meth)acrylate-based polymerizable monomer (f) | HEMA | — | — | — | — | — | — | 25 | — | 25 | 25 |
| Photopolymerization initiator | CQ | 0.3 | — | 0.3 | — | 0.3 | — | 0.3 | — | 0.3 | — |
| Chemical polymerization initiator (oxidizing agent) (d) | THP | — | — | 3 | — | 3 | — | 3 | — | 3 | — |
| | BPO | 3 | — | — | — | — | — | — | — | — | — |
| Chemical polymerization initiator (reducing agent) (d) | PTU | — | — | — | 1 | — | 1 | — | 1 | — | 1 |
| | DEPT | — | 0.4 | — | — | — | — | — | — | — | — |
| Polymerization accelerator (g) | DABE | — | 0.4 | — | 0.4 | — | 0.4 | — | 0.4 | — | 0.4 |
| | TPBSS | — | 0.5 | — | — | — | — | — | — | — | — |
| Polymerization inhibitor | BHT | 0.1 | 0.1 | 0.1 | 0.1 | 0.1 | 0.1 | 0.1 | 0.1 | 0.1 | 0.1 |
| Filler (e) | Inorganic filler 1 | 140 | 140 | 140 | 140 | 140 | 140 | 140 | 140 | 140 | 140 |
| | Inorganic filler 2 | 45 | 45 | 45 | 45 | 45 | 45 | 45 | 45 | 45 | 45 |
| Mixed state of liquid component | | good | good | good | good | good | good | good | good | good | good |
| Tensile bond strength to dentin (unit: MPa) | | 8.4 | | 10.2 | | 9.8 | | 9.0 | | 10.5 | |
| Flexural strength of cured product (unit: MPa) | | 130 | | 122 | | 120 | | 111 | | 102 | |

As shown in Table 1, each of the dental cements of the present invention (Examples 1 to 10) had a homogeneous composition, exhibited a tensile bond strength of 5.8 MPa or more to dentin, and further exhibited a flexural strength of 100 MPa or more when it cured to form a cured product. In addition, it was confirmed that the dental cements of the present invention have the following advantages. As shown in Examples 1 to 6, even a dental cement containing no hydrophilic monofunctional polymerizable monomer (f) can exhibit a high tensile bond strength as shown in Table 1 above and can further exhibit a high flexural strength as shown in Table 1 above when it cures to form a cured product. As shown in Examples 7 to 9, even a dental cement containing a hydrophilic monofuctional polymerizable monomer (f) can exhibit a high tensile bond strength as shown in Table 1 above and can further exhibit a high flexural strength as shown in Table 1 above when it cures to form a cured product, without the need for a large amount of the hydrophilic monofunctional polymerizable monomer (f) (the content of the hydrophilic monofunctional polymerizable monomer (f) is 12.5 parts by weight in 100 parts by weight of the total polymerizable monomers in each dental cement), which means that various compositions can be prepared for the dental cement of the present invention with few limitations.

Comparative Example 1

All the components shown in Table 2 except for the filler (e) (powder) were mixed at ordinary temperature, and the mixed states of the resulting liquid components were tested by the method described above. Subsequently, the homogeneous liquid components thus obtained were each mixed with the filler (e) (powder) to prepare a paste A and a paste B. Next, these pastes were mixed at a mass ratio of 1:1 to prepare a dental cement, and then the tensile bond strength to dentin, and the flexural strength of the cured product were measured by the procedures described above. Table 2 shows the content (parts by weight) of each component of this dental cement and the test results.

Comparative Example 2

ErMA was used as a hydrophilic multifunctional (meth)acrylate-based polymerizable monomer instead of MAEA used in Example 1 as an asymmetric acrylamide-methacrylic acid ester compound (a), and all the components shown in Table 2 except for the filler (e) (powder) were mixed at ordinary temperature, and the mixed states of the resulting liquid components were tested by the method described above. However, ErMA as a hydrophilic multifunctional (meth)acrylate-based polymerizable monomer did not dissolve and thus a dental cement could not be prepared.

Comparative Example 3

EDMA was used as a hydrophilic multifunctional (meth)acrylate-based polymerizable monomer instead of MAEA used in Example 1 as an asymmetric acrylamide-methacrylic acid ester compound (a), and all the components shown in Table 2 except for the filler (e) (powder) were mixed at ordinary temperature, and the mixed states of the resulting liquid components were tested by the method described above. However, EDMA as a hydrophilic multifunctional (meth)acrylate-based polymerizable monomer did not dissolve and thus a dental cement could not be prepared.

Comparative Example 4

BAAE was used as a symmetric (meth)acrylamide-based polymerizable monomer instead of MAEA used in Example 1 as an asymmetric acrylamide-methacrylic acid ester compound (a), and all the components shown in Table 2 except for the filler (e) (powder) were mixed at ordinary temperature, and the mixed states of the resulting liquid components were tested by the method described above. However, BAAE as a symmetric (meth)acrylamide-based polymerizable monomer did not dissolve and thus a dental cement could not be prepared.

Comparative Example 5

DEPBAA was used as a symmetric (meth)acrylamide-based polymerizable monomer instead of MAEA used in Example 1 as an asymmetric acrylamide-methacrylic acid ester compound (a), and all the components shown in Table 2 except for the filler (e) (powder) were mixed at ordinary temperature, and the mixed states of the resulting liquid components were tested by the method described above. Subsequently, the homogeneous liquid components thus obtained were each mixed with the filler (e) (powder) to prepare a paste A and a paste B. Next, these pastes were mixed at a mass ratio of 1:1 to prepare a cement composition, and then the tensile bond strength to dentin of the composition and the flexural strength of the cured product were measured by the procedures described above. Table 2 shows the content (parts by weight) of each component of this dental cement and the test results.

Comparative Examples 6 and 7

All the components shown in Table 2 except for the filler (e) (powder) were mixed at ordinary temperature, and the mixed states of the resulting liquid components were tested by the method described above. Subsequently, the homogeneous liquid components thus obtained were each mixed with the filler (e) (powder) to prepare a paste A and a paste B. Next, these pastes were mixed at a mass ratio of 1:1 to prepare a cement composition, and then the tensile bond strength to dentin of the composition and the flexural strength of the cured product were measured by the procedures described above. Table 2 shows the content (parts by weight) of each component of this dental cement and the test results.

TABLE 2

| | | Com. Ex. 1 | | Com. Ex. 2 | | Com. Ex. 3 | | Com. Ex. 4 | |
|---|---|---|---|---|---|---|---|---|---|
| | | A | B | A | B | A | B | A | B |
| Asymmetric acrylamide-methacrylic acid ester compound (a) | MAEA | 20 | 20 | — | — | — | — | — | — |
| Hydrophilic multifunctional (meth)acrylate-based polymerizable monomer | ErMA | — | — | 20 | 20 | — | — | — | — |
| | EDMA | — | — | — | — | 20 | 20 | — | — |
| Symmetric (meth)acrylamide-based polymerizable monomer | BAAE | — | — | — | — | — | — | 20 | 20 |
| | DEPBAA | — | — | — | — | — | — | — | — |
| Acid group-containing (meth)acrylic polymerizable monomer (b) | MDP | — | — | 10 | — | 10 | — | 10 | — |
| Hydrophobic crosslinkable polymerizable monomer (c) | Bis-GMA | 20 | 20 | 20 | 20 | 20 | 20 | 20 | 20 |
| | D-2.6E | 25 | 35 | 25 | 35 | 25 | 35 | 25 | 35 |
| | TEGDMA | 35 | 25 | 25 | 25 | 25 | 25 | 25 | 25 |
| Hydrophilic monofunctional (meth)acrylate-based polymerizable monomer (f) | HEMA | — | — | — | — | — | — | — | — |
| Photopolymerization initiator | CQ | 0.3 | — | 3 | — | 3 | — | 0.3 | — |
| Chemical polymerization initiator (oxidizing agent) (d) | THP | 3 | — | — | 1 | — | 1 | 3 | — |
| Chemical polymerization initiator (reducing agent) (d) | PTU | — | 1 | — | 1 | — | 1 | — | 1 |
| Polymerization accelerator (g) | DABE | — | 0.4 | — | 0.4 | — | 0.4 | — | 0.4 |
| Polymerization inhibitor | BHT | 0.1 | 0.1 | — | — | — | — | 0.1 | 0.1 |
| Filler (e) | Inorganic filler 1 | 140 | 140 | 140 | 140 | 140 | 140 | 140 | 140 |
| | Inorganic filler 2 | 45 | 45 | 45 | 45 | 45 | 45 | 45 | 45 |
| Mixed state of liquid component | | good | good | poor | poor | poor | poor | poor | poor |
| Tensile bond strength to dentin (unit: MPa) | | 0 | | — | | — | | — | |
| Flexural strength of cured product (unit: MPa) | | 114 | | — | | — | | — | |

| | | Com. Ex. 5 | | Com. Ex. 6 | | Com. Ex. 7 | |
|---|---|---|---|---|---|---|---|
| | | A | B | A | B | A | B |
| Asymmetric acrylamide-methacrylic acid ester compound (a) | MAEA | — | — | — | — | — | — |
| Hydrophilic multifunctional (meth)acrylate-based polymerizable monomer | ErMA | — | — | 20 | 20 | — | — |
| | EDMA | — | — | — | — | — | — |
| Symmetric (meth)acrylamide-based polymerizable monomer | BAAE | — | — | — | — | 20 | 20 |
| | DEPBAA | 20 | 20 | — | — | — | — |
| Acid group-containing (meth)acrylic polymerizable monomer (b) | MDP | 10 | — | 10 | — | 10 | — |

TABLE 2-continued

| | | | | | | | |
|---|---|---|---|---|---|---|---|
| Hydrophobic crosslinkable polymerizable monomer (c) | Bis-GMA | 20 | 20 | 20 | 20 | 20 | 20 |
| | D-2.6E | 25 | 35 | 25 | 35 | 25 | 35 |
| | TEGDMA | 25 | 25 | — | — | — | — |
| Hydrophilic monofunctional (meth)acrylate-based polymerizable monomer (f) | HEMA | — | — | 25 | 25 | 25 | 25 |
| Photopolymerization initiator | CQ | 0.3 | — | 0.3 | — | 0.3 | — |
| Chemical polymerization initiator (oxidizing agent) (d) | THP | 3 | — | 3 | — | 3 | — |
| Chemical polymerization initiator (reducing agent) (d) | PTU | — | 1 | — | 1 | — | 1 |
| Polymerization accelerator (g) | DABE | — | 0.4 | — | 0.4 | — | 0.4 |
| Polymerization inhibitor | BHT | 0.1 | 0.1 | 0.1 | 0.1 | 0.1 | 0.1 |
| Filler (e) | Inorganic filler 1 | 140 | 140 | 140 | 140 | 140 | 140 |
| | Inorganic filler 2 | 45 | 45 | 45 | 45 | 45 | 45 |
| Mixed state of liquid component | | good | good | good | good | good | good |
| Tensile bond strength to dentin (unit: MPa) | | 2.4 | | 5.6 | | 6.1 | |
| Flexural strength of cured product (unit: MPa) | | 121 | | 71 | | 76 | |

As shown in Table 2, the dental cement of Comparative Example 1 containing no acid group-containing (meth)acrylic polymerizable monomer (b) did not exhibit adhesiveness to dentin. In Comparative Examples 2 and 3, since a hydrophilic multifunctional (meth)acrylate-based polymerizable monomer was used instead of the asymmetric acrylamide-methacrylic acid ester compound (a) used in the present invention, the compatibility of ErMA or EDMA with other components was poor and thus the resulting composition was inhomogeneous. As a result, a dental cement could not be prepared. In Comparative Example 4, since BAAE as a symmetric (meth)acrylamide-based polymerizable monomer was used instead of the asymmetric acrylamide-methacrylic acid ester compound (a) used in the present invention, the compatibility of BAAE with other components was poor and thus the resulting composition was inhomogeneous. As a result, a dental cement could not be prepared. In Comparative Example 5 in which DEPBAA as a symmetric (meth)acrylamide-based polymerizable monomer was used instead of the asymmetric acrylamide-methacrylic acid ester compound (a) used in the present invention, a homogeneous composition was obtained, but the tensile bond strength was 2.4 MPa. In Comparative Example 6 in which ErMA as a hydrophilic multifunctional (meth)acrylate-based polymerizable monomer was used instead of the asymmetric acrylamide-methacrylic acid ester compound (a) used in the present invention, a homogeneous composition was obtained because HEMA as a hydrophilic monofunctional (meth)acrylate-based polymerizable monomer was also used in combination, but the flexural strength was 71 MPa. Also in Comparative Example 7 in which BAAE as a symmetric (meth)acrylamide-based polymerizable monomer was used instead of the asymmetric acrylamide-methacrylic acid ester compound (a) used in the present invention, a homogeneous composition was obtained because HEMA as a hydrophilic monofunctional (meth)acrylate-based polymerizable monomer was also used in combination, but the flexural strength was 76 MPa.

INDUSTRIAL APPLICABILITY

The dental cement according to the present invention exhibits excellent adhesiveness to dentin and high mechanical strength, and can be particularly suitably used as a self-adhesive dental cement.

The invention claimed is:
1. A multi-part dental cement, comprising:
an asymmetric acrylamide-methacrylic acid ester compound (a);
an acid group-containing (meth)acrylic polymerizable monomer (b);
a hydrophobic crosslinkable polymerizable monomer (c);
a chemical polymerization initiator (d); and
a filler (e),
wherein the asymmetric acrylamide-methacrylic acid ester compound (a) has formula (1):

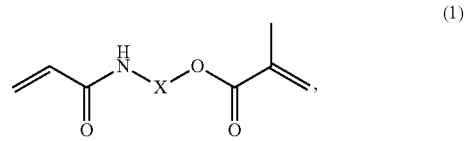

wherein X is an optionally substituted, linear or branched $C_1$ to $C_6$ aliphatic group or an optionally substituted aromatic group,
the aliphatic group is optionally interrupted by at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$—, and
R$^1$ is a hydrogen atom or an optionally substituted, linear or branched $C_1$ to $C_6$ aliphatic group.
2. The multi-part dental cement according to claim 1, wherein X is an optionally substituted, linear or branched $C_1$ to $C_4$ aliphatic group.
3. The multi-part dental cement according to claim 1, comprising 2 to 50 parts by weight of the asymmetric acrylamide-methacrylic acid ester compound (a) 1 to 50 parts by weight of the acid group-containing (meth)acrylic polymerizable monomer (b), and 30 to 95 parts by weight of the hydrophobic crosslinkable polymerizable monomer (c), in 100 parts by weight of all polymerizable monomers.
4. The multi-part dental cement according to claim 1, further comprising a hydrophilic monofunctional polymerizable monomer (f).
5. The multi-part dental cement according to claim 4, wherein the hydrophilic monofunctional polymerizable monomer (f) is at least one selected from the group consisting of a monofunctional (meth)acrylamide-based polymerizable monomer, 2-hydroxyethyl (meth)acrylate, 2,3-dihydroxypropyl (meth)acrylate, and diacetone (meth)acrylamide,
wherein the monofunctional (meth)acrylamide-based polymerizable monomer has formula (2):

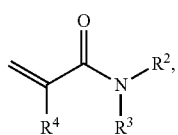
(2)

wherein $R^2$ and $R^3$ are each independently an optionally substituted, linear or branched $C_1$ to $C_3$ alkyl group, and $R^4$ is a hydrogen atom or a methyl group.

6. The multi-part dental cement according to claim 4, wherein the hydrophilic monofunctional polymerizable monomer (f) is a monofunctional (meth)acrylamide-based polymerizable monomer having formula (2):

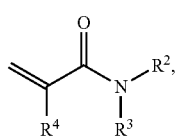
(2)

wherein $R^2$ and $R^3$ are each independently an optionally substituted, linear or branched $C_1$ to $C_3$ alkyl group, and $R^4$ is a hydrogen atom or a methyl group.

7. The multi-part dental cement according to claim 4, wherein the hydrophilic monofunctional polymerizable monomer (f) is included in an amount of 1 to 30 parts by weight in 100 parts by weight of all polymerizable monomers.

8. The multi-part dental cement according to claim 4, comprising 2 to 50 parts by weight of the asymmetric acrylamide-methacrylic acid ester compound (a), 1 to 50 parts by weight of the acid group-containing (meth)acrylic polymerizable monomer (b), 30 to 95 parts by weight of the hydrophobic crosslinkable polymerizable monomer (c), and 1 to 30 parts by weight of the hydrophilic monofunctional polymerizable monomer (f), in 100 parts by weight of all polymerizable monomers.

9. The multi-part dental cement according to claim 1, comprising 5 to 40 parts by weight of the asymmetric acrylamide-methacrylic acid ester compound (a), 2 to 30 parts by weight of the acid group-containing (meth)acrylic polymerizable monomer (b), and 40 to 85 parts by weight of the hydrophobic crosslinkable polymerizable monomer (c), in 100 parts by weight of all polymerizable monomers.

10. The multi-part dental cement according to claim 1, comprising 10 to 30 parts by weight of the asymmetric acrylamide-methacrylic acid ester compound (a), 4 to 20 parts by weight of the acid group-containing (meth)acrylic polymerizable monomer (b), and 50 to 80 parts by weight of the hydrophobic crosslinkable polymerizable monomer (c), in 100 parts by weight of all polymerizable monomers.

11. The multi-part dental cement according to claim 1, wherein the chemical polymerization initiator (d) comprises an oxidizing agent and a reducing agent.

12. The multi-part dental cement according to claim 11, comprising a first part and a second part separated from the first part, wherein the first part includes the oxidizing agent and the second part includes the reducing agent.

* * * * *